May 28, 1974 H. C. SWIM ET AL Plant Pat. 3,559
ROSE PLANT
Filed Feb 12, 1973
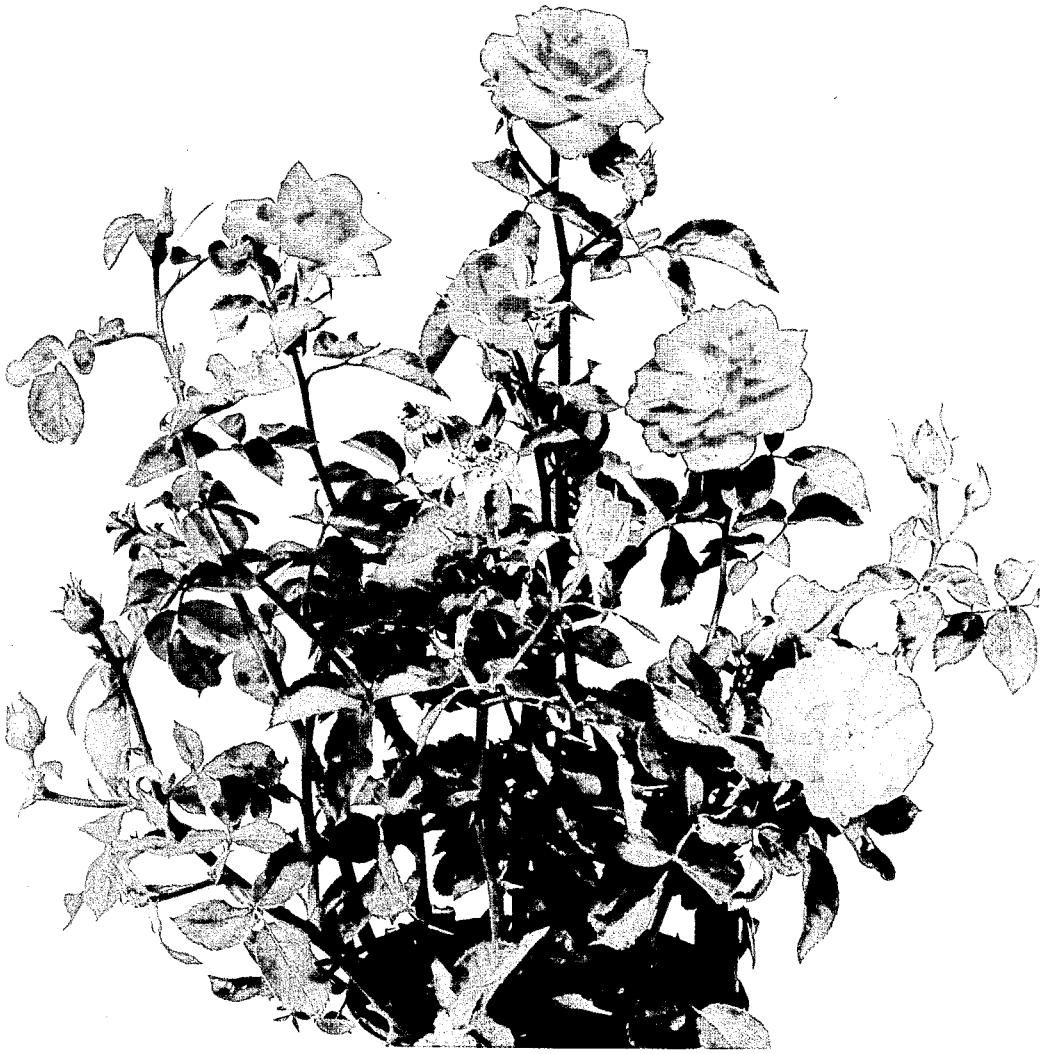

United States Patent Office

Plant Pat. 3,559
Patented May 28, 1974

3,559
ROSE PLANT

Herbert C. Swim and O. L. Weeks, Ontario, Calif., assignors to O. L. Weeks, doing business as Weeks Wholesale Rose Grower, Ontario, Calif.

Filed Feb. 12, 1973, Ser. No. 331,513
Int. Cl. A01h 5/00
U.S. Cl. Plt.—28 1 Claim The present invention relates to a new and distinct variety of rose plant of the floribunda class, which was originated by us by crossing the rose variety known as "Escort" (Plant Pat. No. 2,436) with the rose variety known as "Orange Garnet" (Plant Pat. No. 2,710), the former being the seed parent and the latter being the pollen parent.

As the result of this breading, we have produced a new and improved rose variety which is distinguished from its parents, as well as from all other rose varieties of which we are aware, as evidenced by the following unique combination of principal characteristics which are outstanding in the new variety:

(1) An unusually compact and vigorous habit of growth, with the plant being completely clothed with abundant and attractive foliage;
(2) A completely symmetrical appearance of the blooms and the absence of spikes or other outgrowth which disturbs the symmetry of the plant, unlike other floribundas which are usually less symetrical;
(3) A uniform flower size when the flowers open, which compliments the symmetry and adds to the beauty of the plant and flowers; and
(4) A distinctive and attractive bright red flower color falling between a strong red and a vivid red color, which remains substantially the same color from the bud stage to the open flower stage.

In comparison with its pollen parent "Orange Garnet," our new rose variety is much more compact and symmetrical in habit and bunchier and fuller in form than the parent variety; the foliage is somewhat lighter green in color, with the leaflets being obtuse at their apex contrary to the rounded apex form of the leaflets of the parent; the new variety is less susceptible to powdery mildew; and the plant blooms more continuously and more abundantly throughout the blooming season than the pollen parent.

As compared with the seed parent, "Escort," our new variety bears more flowers in clusters, with a mass blooming effect that is more typical of a floribunda habit contrary to the seed parent which produces more single blooms, with smaller individual buds that are more suitable for forcing for cut flowers; and our new variety is more suitable for outdoor uses for landscape color effects.

Asexual reproduction of our new variety by budding, as performed at Chino, California, shows that the aforementioned characteristics and distinctions come true to form and are established and transmitted through succeeding propagations.

The accompanying drawing shows typical specimens of the vegetative growth and flowers of our new variety in different stages of development and as depicted in color as nearly true as it is reasonably possible to make the same in a color illustration of this character.

The following is a detailed description of our new variety, with color terminology in accordance with the Nickerson Color Fan, published by Munsell Color Company, Incorporated, of Baltimore, Maryland, except where general color terms of ordinary dictionary significance are obvious:

Type: Hardy; dwarf; bush; outdoor; seedling; for cut flowers and for garden decoration.

Class: Hybrid floribunda.
Breeding: Seedling.
*Seed parent.*—"Escort."
*Pollen parent.*—"Orange Garnet."
Propagation: Holds its distinguishing characteristics through succeeding propagations by budding.

FLOWERS

Locality where grown and observed: Ontario, California.
Flowers borne: Both singly and in regular, flat, rounded to pyramidal clusters of from 3 to 5 to stem; on short stems of normal strength.
Quantity of bloom: Free and abundant, both outdoors and in greenhouse.
Continuity: One season; intermittent to continuous.
Fragrance: None.
Bud:
*Peduncle*—Short; slender caliper; erect; stiff; entirely smooth. Color—Light green, with some reddish color.
*Before calyx breaks*—Size—Small. Form—Short; oval to globular; with a conspicuous neck; with foliaceous appendages on the surface of the bud; with slender, bristle-like foliaceous parts extending beyond the tip of the bud equal to ½ to ¾ or more of its length.
*As calyx breaks*—Color—Between Strong Red, Hue 5 R 4/12 and Vivid Red, Hue 5 R 5/13, but darker than latter.
*As first petal opens*—Size—Very small. Form—Mostly globular. Color—Outside—Small basal segment between Brilliant Yellow Green, Hue 2.5 GY 8/9 and Brilliant Yellow Green, Hue 2.5 GY 9/8, blending into between Vivid Red, Hue 5 R 5/13 and Strong Red, Hue 5 R 4/12, but brighter. Inside—Small basal segment between Brilliant Yellow Green, Hue 2.5 GY 8/9 and Brilliant Yellow Green, Hue 2.5 GY 9/8, blending into between Strong Red, Hue 5 R 4/12 and Vivid Red, Hue 5 R 5/13, but brighter.
*Opening*—Opens up well.
Bloom:
*Size (when fully open)*—Small; from 1¾ inches to 2½ inches.
*Petalage*—Double (more petals, but stamens not hidden); from 24 to 30 pellets; arranged regularly.
*Form*—High-centered at first, but becoming open; petals at first being tightly cupped and rolled outward, but later becoming tightly flat and rolled outward at maturity.
Petals:
*Texture*—Thick; soft.
*Appearance*—Inside—Velvety. Outside—Satiny.
*Shape*—Outside—Mostly round, with apex flat. Intermediate—Round, with apex flat. Inside—Somewhat ovate, with apex flat.

This description was made from a rose grown outdoors in the month of October at Ontario, California:

*Color*—Outer petal—Outside surface—Small basal segment of Brilliant Yellow Green, Hue 2.5 GY 9/8, but brighter, blending into between Strong Red, Hue 5 R 4/12 and Vivid Red, Hue 5 R 5/13, but brighter. Inside surface—Small basal segment of Brilliant Yellow Green, Hue 2.5 GY 9/8, but brighter, blending into Strong Red, Hue 5 R 4/12 and Vivid Red, Hue 5 R 5/13, but brighter. Intermediate petal—Outside surface—Small basal segment of Brilliant Yellow Green, Hue 2.5 GY 9/8, but brighter, blending into Strong Red, Hue 2.5 R 5/12 and Vivid Red, Hue 5 R 5/13, but brighter. Inside surface—Small basal segment of Brilliant Yellow Green, Hue 2.5 GY 9/8, but brighter, blending into Strong Red, Hue 5 R 4/12 and Vivid Red, Hue 5 R 5/13, but brighter. Inner petal—Outside surface—Small basal segment of Brilliant Yellow Green, Hue 2.5 GY 9/8, but brighter, blending into Strong Red, Hue 5 R 4/12 and Strong Red, Hue 2.5 R 5/12, but brighter. Inside surface—Small basal segment of Brilliant Yellow Green, Hue 2.5 GY 9/8, but brighter, blending into between Strong Red, Hue 5 R 4/12 and Vivid Red, Hue 5 R 5/13, but brighter.

This description was made from a rose that was open for three days outdoors during the month of October at Ontario, California:

*Color.*—Outer petal—Outside surface — Between Strong Red, Hue 2.5 R 5/12 and Strong Red, Hue 5 R 4/12, but much brighter, with a small basal segment of Brilliant Yellow Green, Hue 2.5 GY 9/8, but lighter. Inside surface—Small basal segment of Brilliant Yellow Green, Hue 2.5 GY 9/8, but somewhat lighter, blending at middle of petal into between Strong Red, Hue 2.5 R 5/12 and Strong Red, Hue 2.5 R 4/12, then further blending toward apex of Dark Red, Hue 5 R 3/7, but lighter. Inner petal—Outside surface—Between Strong Red, Hue 2.5 R 5/12 and Strong Red, Hue 5 R 4/12, but lighter, with a small basal segment of Brilliant Yellow Green, Hue 2.5 GY 9/8, but lighter. Inside surface—Small basal segment of Brilliant Yellow Green, Hue 2.5 GY 9/8, but lighter, blending at middle of petal into Strong Red, Hue 5 R 4/12, and blending further toward apex into Dark Red, Hue 5 R 3/7, but lighter.

*General color effect.*—Newly opened flower—Between Strong Red, Hue 5 R 4/12 and Vivid Red, Hue 5 R 5/13, but brighter. 3-days open—Between Strong Red, Hue 5 R 4/12 and Vivid Red, Hue 5 R 5/13, but darker.

*Behavior*—Drop off cleanly.

*Flower longevity.*—On bush in garden—5 days in October. Cut roses grown outdoors and kept at living room temperatures—5 days in October.

REPRODUCTIVE ORGANS

Stamens: From few to medium number; arranged irregularly about pistils; tucked in calyx.

Filaments: Short.

*Color.*—Some yellow and others pale reddish.

Anthers: From medium to large size; all open at once.

*Color.*—Yellowish.

Pollen: From sparse to moderate abundance.

*Color.*—Yellowish.

Pistils: Very few.

Styles: Very uneven; very short; very thin caliper; loosely separated.

Stigma:

*Color.*—Reddish.

Ovaries: All enclosed in calyx.

Hips: None observed.

Sepals: Permanent; short; spear-shaped; recurved.

*Color.*—Medium green, with some reddishness.

Seeds: None observed.

PLANT

Foliage:

*Leaves.*—Compound of 3, 5 or 7 leaflets; very abundant; small; moderately glossy.

*Leaflets.*—Many. Shape—Ovate. Apex — Acute; Base—Elliptical. Margin—Finely serrate.

*Color.*—Mature—Upper surface—moderately dark green. Under surface—Moderately light green, with reddish veins. Young—Upper surface—Moderately dark green, with dark reddish border. Under surface—Primarily reddish, with some light green showing in middle portion.

*Rachis (the supporting stem of the compound leaf).*—From light to medium weight. Upper side —Smooth. Under side—Moderately prickly.

*Stipules.*—Moderately short; moderately narrow; with points of medium length turning out at an angle of more than 45°; recurved toward the stem.

*Disease resistance.*—Better than average resistance to powdery mildew, and average resistance to other common rose diseases, as determined from comparison with other rose varieties grown under the same conditions at Ontario, California.

Growth:

*Habit.*—Low-growing; bushy; much branched.

*Growth.*—Free and vigorous.

*Canes.*—Moderately light.

*Main stems.*—Color—Dull green. Large prickles—Few; medium long; mostly straight; with short, somewhat round base; color—brown. Small prickles—Few; color—brown. Hairs—None.

*Branches.*—Color—Grey-green, with some reddish at base. Large prickles—From none to few; from medium length to long; straight; with short, elongated base; color—Red. Small prickles—None. Hairs—None.

*New shoots.*—Color—From bronze to red. Large prickles—From none to few; color—primarily reddish, but some with green shading. Small prickles—None. Hairs—None.

We claim:

1. A new and distinct variety of rose plant of the floribunda class, substantially as herein shown and described, characterized particularly as to novelty by the unique combination of an unusually compact and vigorous habit of growth, with the plant being completely clothed with abundant and attractive foliage, a completely symmetrical appearance of the blooms and the absence of spikes or other outgrowth which disturbs the symmetry of the plant, unlike other floribundas which are usually less symmetrical, a uniform flower size when the flowers open, which compliments the symmetry and adds to the beauty of the plant and flowers, and a distinctive and attractive bright red flower color falling between a strong red and a vivid red color, which remains substantially the same color from the bud stage to the open flower stage.

No references cited.

ROBERT E. BAGWILL, Primary Examiner